United States Patent [19]

Ozaki et al.

[11] Patent Number: 5,130,240
[45] Date of Patent: Jul. 14, 1992

[54] PROCESS FOR PRODUCING D-ALPHA-ALANINE AND/OR L-ALPHA-ALANINEAMIDE BY *ARTHROBACTER SP*

[75] Inventors: Akio Ozaki; Hideki Kawasaki; Yukio Hashimoto; Keishiro Tamura, all of Hofu; Keiko Ochiai, Sagamihara; Isao Kawamoto, Hiratsuka, all of Japan

[73] Assignee: Kyowa Hakko Kogyo Co., Ltd., Tokyo, Japan

[21] Appl. No.: 711,355

[22] Filed: Jun. 4, 1991

Related U.S. Application Data

[63] Continuation of Ser. No. 327,000, Mar. 22, 1989, abandoned.

[30] Foreign Application Priority Data

Mar. 24, 1988 [JP] Japan ................................. 63-70217

[51] Int. Cl.$^5$ .......................... C12P 13/06; C12N 9/78; C12N 1/20
[52] U.S. Cl. ................................. 435/116; 435/252.1; 435/227; 435/228; 435/280
[58] Field of Search ................. 435/116, 227, 228, 280, 435/252.1, 830

[56] References Cited

U.S. PATENT DOCUMENTS

| | | | |
|---|---|---|---|
| 3,239,428 | 3/1966 | Toyokawa et al. | 435/830 X |
| 3,871,959 | 3/1975 | Chibata et al. | 435/116 |
| 3,971,700 | 7/1976 | Boesten | 435/280 |
| 4,366,250 | 12/1982 | Jallageas et al. | 435/280 |
| 4,370,414 | 1/1983 | Mitsugi et al. | 435/830 X |
| 4,705,752 | 11/1987 | Boesten et al. | 435/116 X |

FOREIGN PATENT DOCUMENTS

| | | |
|---|---|---|
| 0181675 | 11/1985 | European Pat. Off. |
| 184392 | 9/1985 | Japan |
| 274690 | 12/1986 | Japan |
| 55097 | 3/1987 | Japan |
| 87998 | 4/1988 | Japan |

OTHER PUBLICATIONS

Asano, Y., et al. 1988, "Enzymatic Synthesis of D-amino acid amides (I)," *Nippon Nogei Kagaku Kaisha*, vol. 62 (3) p. 352. (English translation).
Foster, D. L., and Fillingame, R. H. 1979. "Energy-transducing ATPase of *Escherichia coli*". *Journal of Biological Chemistry*, vol. 254 (17) pp. 8230–8236.
Goodfellow, M., and Cross, T. "Classification". In *The Biology of the Actinomycetes*, Ed. Goodfellow, M., et al. 1984 Academic Press, London. pp. 40–44.
Patent Abstracts of Japan, vol. 11, No. 13 (2460).

*Primary Examiner*—Douglas W. Robinson
*Assistant Examiner*—Marian C. Knode
*Attorney, Agent, or Firm*—Fitzpatrick, Cella, Harper & Scinto

[57] ABSTRACT

A novel D-amidase is described. The enzyme specifically hydrolyzes D-α-alanineamide into D-α-alanine. It is produced by culturing a microorganism belonging to the genus Arthrobacter, and is useful as an enzyme for efficiently producing D-α-alanine having a high optical purity and/or L-α-alanineamide from DL-α-alanineamide or D-α-alanineamide at low cost.

13 Claims, 4 Drawing Sheets

PROCESS FOR PRODUCING D-ALPHA-ALANINE AND/OR L-ALPHA-ALANINEAMIDE BY *ARTHROBACTER SP*

This application is a continuation of application Ser. No. 07/327,000 filed Mar. 22, 1989, now abandoned.

BACKGROUND OF THE INVENTION

The present invention relates to a novel enzyme capable of specifically hydrolyzing D-α-alanineamide to produce D-α-alanine (hereinafter referred to as D-amidase) and a process for producing D-α-alanine and/or L-α-alanineamide using the enzyme.

D-α-alanine is an important compound as a sweetening, or a synthetic intermediate or starting compound for synthesizing various physiologically active substances. L-α-Alanineamide is a starting compound for producing L-α-alanine, which is an important amino acid as food and medicines.

The following processes for producing D-α-alanine have been known so far.

(1) A microbiological process for producing D-α-alanine through direct fermentation [Japanese Published Unexamined Patent Application Nos. 22881/76 and 76482/77].

(2) A process for producing D-α-alanine by separating D-α-alanine from DL-α-alanine through the action of microorganism having an ability to decompose only L-α-alanine [Ohshima and Tanaka: *Amino Acid Nucleic Acid*, 15, 89-93 (1966)].

(3) A process for producing D-α-alanine through the action of acylase produced by a microorganism, upon the N-acyl compound of DL-α-alanine and through the successive optical resolution of DL-α-alanine (Japanese Published Examined Patent Application No. 22380/66).

(4) A process for producing D-α-alanine through the action of microorganisms having a hydantoinase activity upon 5-methylhydantoin to form D-(N-carbamoyl)alanine, and by treating D-(N-carbamoyl)alanine chemically or microbiologically [Yamada, et al: Hakko To Kogyo, 38, 937 (1980), Japanese Published Unexamined Patent Application Nos. 91189/78, 89088/79, 88697/80, 104890/80, 114291/80, etc.].

(5) A process for producing D-α-alanine by hydrolyzing D-α-alanineamide through the hydrolytic activity possessed by microorganisms belonging to the genus Bacillus, Bacterium, Micrococcus, Brevibacterium, Achromobacter, Alcaligenes, Kurthia, Pseudomonas, Rhodococcus or Serratia [Japanese Published National Publication No. 500319/81, Japanese Published Unexamined Patent Application Nos. 184392/85, 96989/86 and 274690/86].

(6) A process for producing D-α-amino acid by hydrolyzing DL-α-amino acid amide through the hydrolytic activity specific to D-α-amino acid amide and possessed by microorganisms belonging to the genus Rhodococcus [Japanese Published Unexamined Patent Application No. 87998/88].

(7) A process for producing D-α-alanine through the action of D-amino-acid transaminase upon pyruvic acid [Japanese Published Unexamined Patent Application No. 205790/87].

(8) A process for producing D-α-alanine by the chemical optical resolution through the preferential crystallization of DL-α-alanine p-chlorobenzenesulfonate [Japanese Published Examined Patent Application No. 14369/72 and Japanese Published Unexamined Patent Application No. 57914/73].

Among the aforementioned processes for producing D-α-alanine, the processes (1), (2), (6) and (8) have no or lower D-α-alanine productivity, and the processes (3), (4) and (7) have complicated operations because of the reaction consisting of several stages. The processes (5) and (7) require an expensive optically active substrate and thus raise the cost of production.

The enzymes capable of hydrolyzing D-α-alanineamide are disclosed in Abstracts of 1988th Meeting of the Agricultural Chemical Society of Japan, page 352.

Any process for producing L-α-alanineamide of high optical purity at industrially low cost is unknown yet.

Presently, an enzyme capable of producing D-α-alanine and L-α-alanineamide of high optical purity directly from inexpensive DL-α-alanineamide and a process for producing D-α-alanine and L-α-alanineamide using the enzyme are desired.

Extensive studies have been made on the development of an industrially favorable process for producing D-α-alanine from DL-α-alanineamide. As a result, the present inventors have found that microorganisms belonging to the genus Arthrobacter produce an enzyme capable of specifically hydrolyzing D-α-alanineamide thereby to produce D-α-alanine from DL-α-alanineamide or D-α-alanineamide. Examination of its physicochemical properties after isolation and purification of the enzyme reveals that the enzyme is novel.

SUMMARY OF THE INVENTION

The present invention provides a novel D-amidase as well as a process for producing D-α-alanine and/or L-α-alanineamide, which comprises carrying out an enzymatic hydrolysis in an aqueous medium containing DL-α-alanineamide or D-α-alanineamide in the presence of a culture, cells, a treated product thereof or D-amidase isolated therefrom, of a microorganism belonging to the genus Arthrobacter and capable of producing D-amidase, and recovering D-α-alanine and/or L-α-alanineamide from the resulting reaction mixture.

The physicochemical properties of the novel D-amidase are given below.

1) Activity and substrate specificity: It specifically hydrolyzes D-α-alanineamide into D-α-alanine; the activity of hydrolyzing L-α-alanineamide is 0 to 1.5% of the activity of hydrolyzing D-α-alanineamide.
2) Optimum pH: pH 7 to 8 at 30° C.
3) Optimum temperature: 40° to 45° C. at pH of 7.5
4) Heat stability: It is inactivated when allowed to stand at a temperature above 60° C. for 10 minutes.
5) pH stability: It is stable within a range of pH 6.5 to 10 at 30° C.
6) Molecular weight: 50,000±5,000 (SDS-polyacrylamide electrophoresis)
7) Activation: No coenzyme is required for activation.
8) Isoelectric point: pH 5.2±0.3

DESCRIPTION OF THE INVENTION

Figure 1:
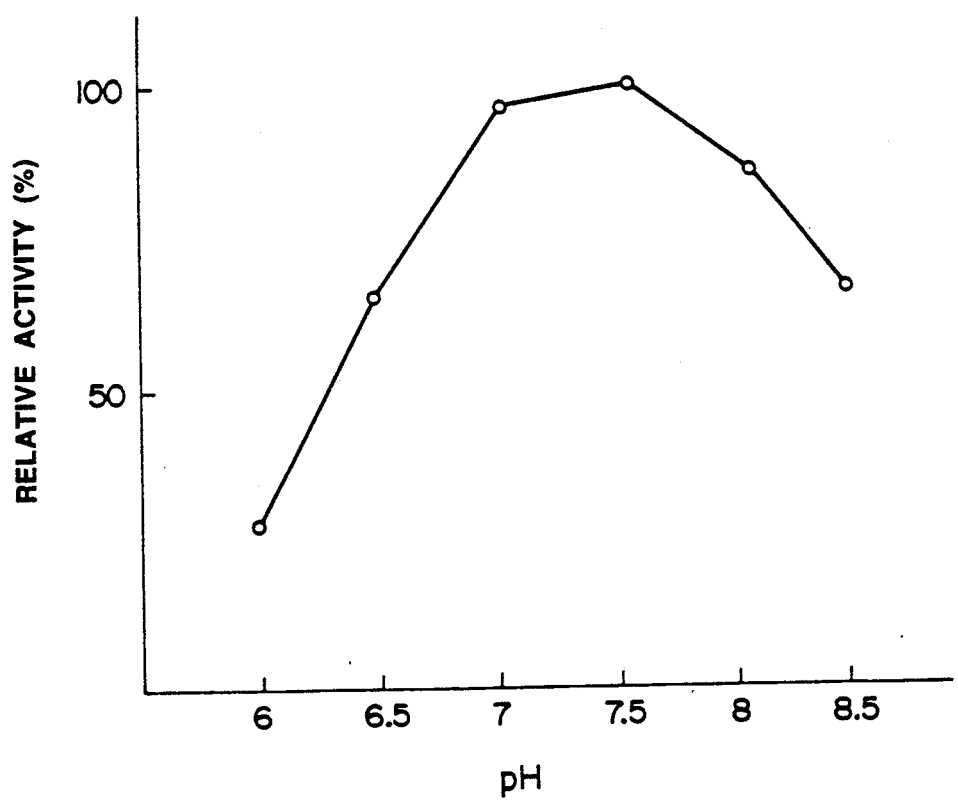
FIG. 1 shows the relative activity with change in pH, when defining the enzyme activity at pH 7.5 as 100%.

Any microorganisms can be used in producing of the enzyme of the present invention, so far as they belong to the genus Arthrobacter and have an ability to produce the enzyme having the properties described above. For example, Arthrobacter sp. H-4904 can be mentioned.

Arthrobacter sp. H-4904 is a microorganism newly isolated from the natural source.

Bacteriological properties of Arthrobacter sp. H-4904 are described below:

(a) Morphology

1) Form and size of cells: Spherical form (0.8–1.0 μm in diameter) and rod form (0.8 μm in diameter and 1.2–1.5 μm long).
Motility: Motile with flagella occurring in polar positions.
3) Spore: none
4) Gram staining: positive
5) Acid resistance: scarcely observed

(b) Growth states on various media

1) Bouillon-agar plate culture forms circular, convex, smooth colonies, showing an opaque, whitish yellow color without formation of diffusible pigments.
2) Bouillon-agar slant culture gives well growth, showing an opaque, whitish yellow color.
3) Bouillon liquid culture gives turbid growth without formation of surface membrane.
4) Bouillon-gelatin stab culture gives no liquefaction.
5) Litmus milk: no reduction of litmus and no coagulation.

(c) Physiological properties

1) Nitrate reduction: positive
2) Denitrification reaction: positive
3) MR test: negative
4) VP test: negative
5) Indole formation: negative
6) Hydrogen sulfide formation: negative
7) Starch hydrolysis: negative
8) Citric acid utilization (Simons' medium): positive
9) Utilization of inorganic nitrogen source
   Nitrate: negative
   Ammonium salt: weakly positive
10) Pigment formation: negative
11) Urease: negative
12) Oxidase: negative
13) Catalase: positive
14) Growth range
   1) pH: 5.0–9.0 (optimum pH: 6.0–8.0)
   2) Temperature: 15°–37° C. (optimum temperature: 30° C.)
15) Oxygen relationship: aerobe or facultative anaerobe
16) OF test: negative
17) Acid and gas formation from saccharides:

|  | Acid | Gas (peptone-water) |
| --- | --- | --- |
| L-arabinose | — | — |
| D-xylose | — | — |
| D-glucose | — | — |
| D-mannose | — | — |
| D-fructose | — | — |
| D-galactose | — | — |
| Maltose | — | — |
| Sucrose | — | — |
| Lactose | — | — |
| Trehalose | — | — |
| D-sorbitol | — | — |
| D-mannitol | — | — |
| Inositol | — | — |
| Glycerine | — | — |
| Starch | — | — |

18) Sodium chloride resistance: grow at 15% NaCl.

(d) Chemical Composition

1) Peptidoglycan-constituting amino acids: lysine, alanine and glutamic acid
2) mol % G+C (Tm): 63.17

The microorganism with the aforementioned bacteriological properties was identified as bacteria belonging to the genus Arthrobacter, referring to Bergey's Manual of Systematic Bacteriology, Vol.2 (1986) on the basis of such properties as gram-positive spherical or rod form; motile with flagella occurring in polar positions, aerobe or facultative anaerobe; non-formation of spores; lysine, alanine and glutamic acid as peptidoglycan-constituting amino acids; mol % G+C of DNA being 63.17. The strain was named Arthrobacter sp. H-4904 and has been deposited with the Fermentation Research Institute (FRI), the Agency of Industrial Science and Technology under the Budapest Treaty since Jan. 14, 1988 with the accession number of FERM BP-1649.

Any of natural media and synthetic media can be used as the medium for culturing the microorganism, so far as they appropriately contain a carbon source, a nitrogen source, inorganic salts, etc. that can be assimilated by the microorganism and that the microorganism having an ability to produce the enzyme of the present invention can be efficiently cultured therein.

As the carbon source, carbohydrates such as glucose, sucrose, molasses, starch hydrolyzate, etc., organic acids such as acetic acid, propionic acid, etc., and alcohols such as ethanol, propanol, etc. can be used.

As the nitrogen source, ammonia, various ammonium salts of inorganic and organic acids such as ammonium chloride, ammonium sulfate, ammonium acetate, ammonium phosphate, etc., amines and other nitrogen-containing compounds, peptone, meat extract, yeast extract, corn steep liquor, casein hydrolyzate, soybean cake hydrolyzate, various fermentation cells and their digested products, etc. can be used.

As the inorganic materials, potassium dihydrogen phosphate, dipotassium hydrogen phosphate, magnesium phosphate, magnesium sulfate, sodium chloride, ferrous sulfate, manganese sulfate, copper sulfate, calcium carbonate, etc. can be used.

Culturing is carried out under aerobic conditions with shaking, submerged aeration stirring, etc. preferably at a temperature of 15° to 37° C., usually for 16–72 hours, while keeping pH at 5.0–9.0 by adding an inorganic or organic acid, an alkaline solution, urea, calcium carbonate, ammonia, etc.

It is necessary to add 0.1–20 g/l D-α-alanineamide, L-α-alanineamide or DL-α-alanineamide to the medium in the culturing, for the purpose of inducing and accumulating D-amidase. By use of an appropriate mutant, D-amidase can be accumulated without adding D-α-alanineamide, L-α-alanineamide or DL-α-alanineamide (which is hereinafter referred to as "inducing substance") to the medium.

The mutant can be obtained from Arthrobacter sp. H-4904 as the parent strain according to the ordinary mutagenesis, for example, through ultraviolet irradiation, radiation irradiation such as X-ray irradiation, treatment with mutation-inducing agent, etc.

After the mutation treatment, a desired mutant can be obtained by recovering colonies growing in an ordinary nutrient medium, for example, a bouillon-yeast extract medium and selecting a strain that accumulates D-amidase in a medium containing no inducing substance.

An example of the thus obtained mutant is Arthrobacter sp. H-7095, which has been deposited with the FRI under the Budapest Treaty since Mar. 2, 1988 with the accession number of FERM BP-1773.

In order to recover and purify the enzyme from the culture, conventional purification methods for an enzyme may be used. For example, the culture is centrifuged and the cells are collected. The collected cells are disrupted by means of mechanical disruption using a DYNO-MILL, French Press, Manton-Gaulin homogenizer, ultrasonication, etc., and the resulting suspension is centrifuged to remove cell debris. The enzyme in the supernatant is isolated and purified by salting-out method using ammonium sulfate, ion exchange chromatography using DEAE-Sepharose, CM-Sepharose, etc., whereby an SDS-polyacrylamide gel electrophoretically pure enzyme can be obtained.

The enzyme activity is determined as follows.

After 1.0 ml of 50 mM phosphate buffer (pH 7.5) containing 250 mM D-α-alanineamide is heated at 30° C. for 5 minutes, 0.1 ml of an enzyme solution is added thereto to carry out incubation at 30° C. for 30 minutes. The reaction is terminated by adding 0.1 ml of 6N hydrochloric acid thereto. The amount of the D-α-alanine formed during the reaction is determined by high performance liquid chromatography (HPLC) under the following conditions.

Column CHIRALPAK WE(-), manufactured by Daicel Ltd.
Eluate: 0.25 mM $CuSO_4$ aqueous solution
Flow rate: 1 ml/min
Column temperature: 45° C.
Method for detection: o-Phthalaldehyde is added to react at 50° C. and fluorescence is detected (excitation wavelength: 344 nm; fluorescent wavelength: 444 nm)

The enzyme activity is defined as 1 unit (U) in terms of the activity for hydrolyzing D-α-alanineamide into 1 μmol of D-α-alanine for a minute under the assay conditions defined above.

The activity for hydrolyzing L-α-alanineamide into L-α-alanine (hereafter referred to as L-amidase activity) can be determined under the conditions described above except that L-α-alanineamide is used in place of D-α-alanineamide.

Though D-α-alanine and/or L-α-alanineamide can be obtained by acting the enzyme of the present invention on DL-α-alanineamide or D-α-alanineamide, it is preferred that an enzymatic hydrolysis is carried out in an aqueous medium containing DL-α-alanineamide or D-α-alanineamide in the presence of a culture, cells or a treated product thereof, of the microorganism belonging to the genus Arthrobacter and capable of producing the enzyme of the present invention, and that D-α-alanine and/or L-α-alanineamide can be recovered from the resulting reaction mixture.

The enzymatic hydrolysis can be carried out either during the culturing of the microorganism or by allowing the culture, cells, a treated product thereof, or the purified enzyme to react DL-α-alanineamide or D-α-alanineamide in an aqueous medium after the completion of culturing.

The treated product of cells of the microorganism having the D-amidase activity includes, for example, dried cells, freeze-dried cells, surfactant-treated cells, enzyme-treated cells, ultrasonically disrupted cells, mechanically disrupted cells, solvent-treated cells, and proteinous fractions of cells, and further includes immobilized products of cells and the aforesaid treated products thereof. Purified D-amidase may be used and may also be used as the immobilized products.

The aqueous medium includes, for example, water, buffer solutions of phosphate, carbonate, acetate, borate, citrate, Tris, etc., alcohols such as methanol, ethanol, propanol, etc., esters such as ethyl acetate, etc., ketones such as acetone, etc., and amides such as acetamide, etc.

When purified enzyme is used in the reaction, it is preferred that 5 to 50% glycerol is added to the aqueous medium in order to improve the stability of the enzyme.

The reaction is carried out usually at a temperature of 15° to 50° C. and pH of 6.0 to 9.5 for 1 to 72 hours. The potency of enzyme in the reaction mixture depends on the amount of DL-α-alanineamide or D-α-alanineamide used and the reaction time, and usually is 1 to 300 kU/l. Specifically, when cells are used in the reaction, the concentration of cells is usually 1 to 50 g/l as wet cells. The DL-α-alanineamide or D-α-alanineamide for use in the reaction can be in any one of free form, hydrochloride form and sulfate form. In case of DL-α-alanineamide, 1–500 g/l, preferably 1–400 g/l can be used, and in case of D-α-alanineamide, 1–300 g/l, preferably 1–200 g/l can be used.

The alanine racemase usually contained in microbial cells is an enzyme that catalyzes racemation of optically active alanine and lowers the optical purity of D-α-alanine formed in the process of the present invention. The microorganism to be used in the present invention has a smaller alanine racemase content, and thus D-α-alanine of satisfactorily optical purity can be obtained by use of the microorganisms of the present invention as such. However, D-α-alanine of much higher optical purity can be obtained by appropriately using well known procedures for suppressing the alanine racemase activity, for example, by obtaining a mutant with no or less alanine racemase activity through an ordinary mutagenesis [J. Wild, et al.: *Mol. Gen. Genet.* 198, 315–322 (1985)]; by inactivating the activity of alanine racemase in the microorganism through a heat treatment, etc. [Takamatsu, Tosa and Chihata *J. Jap. Chem. Soc.* 9 1369 (1983)], and by adding an alanine racemase inhibitor to the aqueous medium during the reaction [*Kagaku To Seibutsu* 20 770–772 (1986); *Seikagaku Jikken Koza* 11 275–296].

When DL-α-alanineamide is used in the enzymatic hydrolysis, D-α-alanine is formed and accumulated in the aqueous medium and concurrently, L-α-alanineamide remains in the aqueous medium after the hydrolysis. Thus, L-α-alanineamide can be obtained by recovering it from the aqueous medium.

D-α-alanine and L-α-alanineamide can be recovered from the culture or the aqueous medium according to an ordinary separation procedure, for example, through column chromatography using ion exchange resin, etc., or through crystallization.

The present invention is described below, referring to Examples.

EXAMPLE 1

At first, 150 ml of BYG medium [a medium containing 2% of bouillon powder (product of Kyokuto Co.), 0.5% of yeast extract (product of Difco), 0.5% of polypeptone and 0.2% of glucose, adjusted to pH 7.2 with 6N NaOH] was poured into each of 2 l-flasks provided with baffles, and sterilized at 120° C. for 20 minutes. Then, one loopful of Arthrobacter sp. H-4904 growing on a bouillon slant was inoculated into each of the media and cultured at 30° C. for 20 hours with shaking. The resulting culture was used as a seed culture.

Separately, a medium containing 3% of glucose, 2% of corn steep liquor, 0.5% of peptone, 1% of NaCl, 2% of $(NH_4)_2SO_4$, 0.3% of $MgSO_4.7H_2O$, 0.001% of $FeSO_4.7H_2O$, 0.0001% of $MnSO_4.7H_2O$ and 0.6% of DL-α-alanineamide and having a pH of 7.2 was prepared, and 18 l of the thus prepared medium was poured into a 30 l-jar fermenter and sterilized at 120° C. for 20 minutes. Then, 2 l of the seed culture was aseptically introduced into the medium and cultured with agitation and aeration (450 rpm, 10 l/min) at 30° C. for 30 hours. The D-amidase activity of the thus obtained culture was 64 U/ml.

The cells obtained by centrifuging the culture were suspended in 1.9 l of 50 mM sodium phosphate buffer (pH 7.5). Then, the cells were disrupted with a DYNO-MILL (laboratory mill model KDL, manufactured by W. A. Bachafen Maschinenfabrik). The cell suspension was centrifuged and the resulting supernatant was subjected to DEAE-Sepharose Fast Flow (manufactured by Pharmacia Inc.) column chromatography which had been equilibrated with 50 mM Tris-hydrochloride buffer (pH 7.5). Then, density gradient elution was carried out using the same buffer in which the rate of sodium chloride was increased from 0 to 0.4M. D-amidase was eluted in the fraction containing 0.2M sodium chloride The active fraction was further subjected to BUTYL TOYOPEARL (TSK-GEL 650° C., manufactured by Toyo Soda Mfg. Co., Ltd.) column chromatography which had been equilibrated with 50 mM Tris-hydrochloride buffer (pH 7.5) containing 20% saturated ammonium sulfate. Then, density gradient elution was carried out using the same buffer in which the rate of saturated ammonium sulfate was decreased from 20% to 0.1%. D-amidase was eluted in the 15 to 10% saturated ammonium sulfate fractions. After desalting the active fraction with UF membrane (SIP-1013, manufactured by Asahi Chemical Co., Ltd.), glycerol was added to the active fraction in a concentration of 25% (v/v). The fraction was then subjected to DEAE-Trisacryl LS (manufactured by Reactifs IBF Soc. Chim) column chromatography which had been equilibrated with 50 mM Tris-hydrochloride buffer (pH 7.5) containing 25% (v/v) glycerol. Then, density gradient elution was carried out using the same buffer in which the rate of sodium chloride was increased from 0 to 0.4M. D-amidase was eluted in the fractions containing 0.2M sodium chloride.

The D-amidase activity of the thus obtained enzyme was $6.0 \times 10^4$ U. The enzyme showed a single band of molecular weight of about 50,000 in SDS-polyacrylamide gel electrophoresis.

The specific activity and Km value of the enzyme to D-α-alanineamide and L-α-alanineamide are shown in Table 1.

TABLE 1

|  | D-α-Alanineamide | L-α-Alanineamide |
|---|---|---|
| Specific Activity (U/mg protein) | 1800 | 17.4 |
| Km (mM) | 4.2 | 26.1 |

In FIG. 1, the activity with change in pH is shown in terms of relative activity, when defining the enzyme activity at pH 7.5 as 100%. The enzyme had the optimum pH of 7 to 8 at 30° C.

Figure 2:
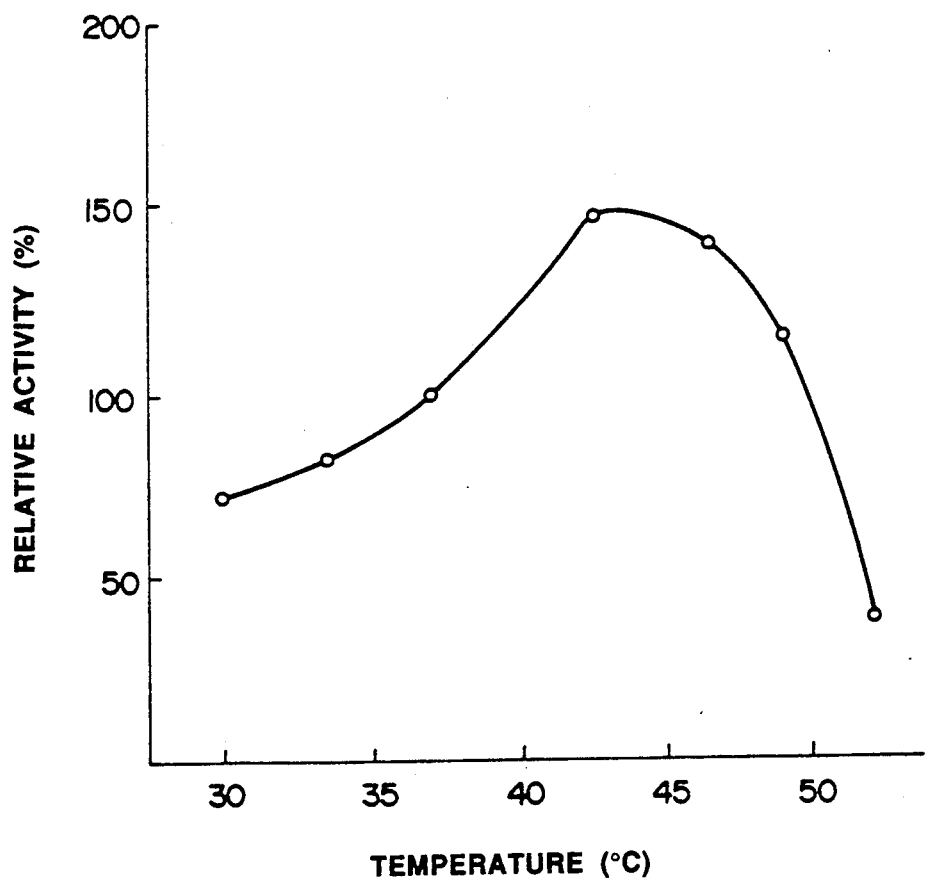
FIG. 2 shows the relative activity with change in temperature, when defining the enzyme activity at 37° C. as 100%.

In FIG. 2, the activity with change in temperature is shown in terms of relative activity, when defining the enzyme activity at 37° C. as 100%. As shown in FIG. 2, the enzyme had the optimum temperature of 40° to 45° C. at pH 7.5.

The pH stability of the enzyme was determined by the following method.

Figure 3:
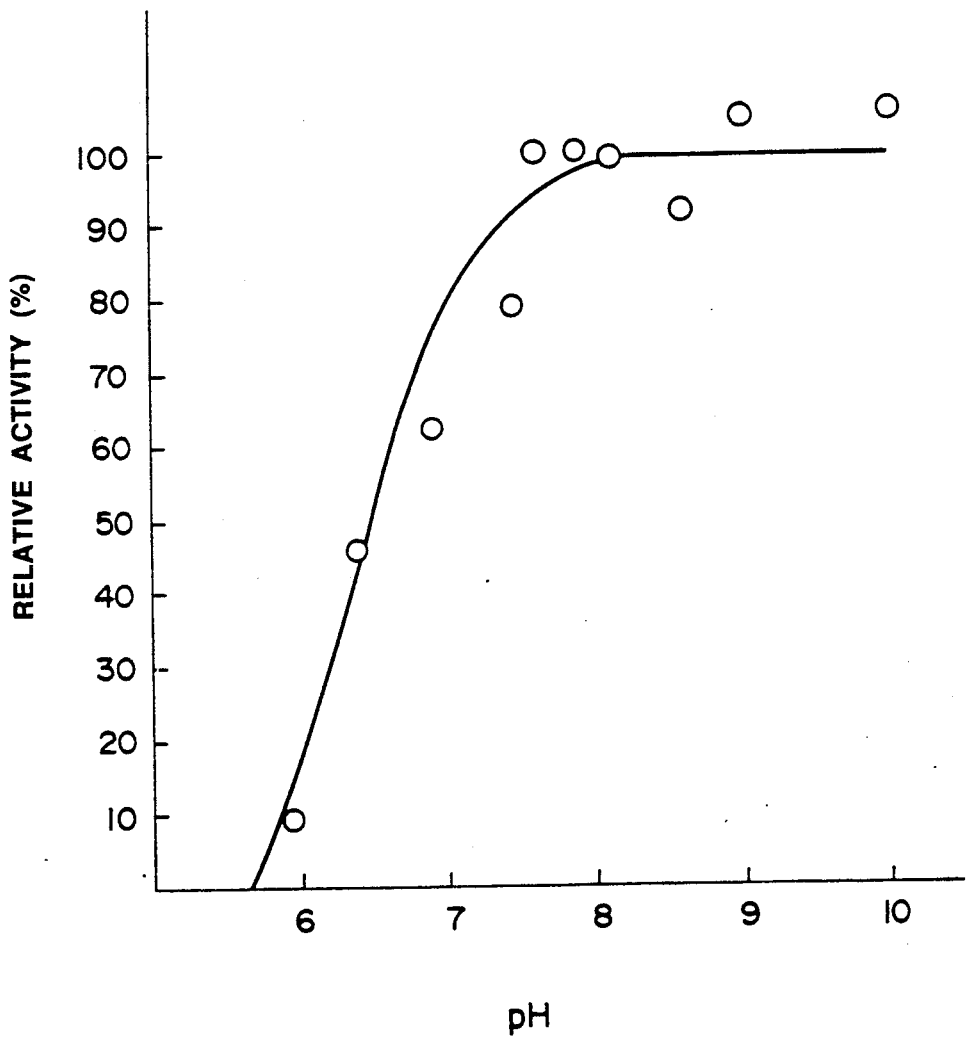
FIG. 3 shows the pH stability of the enzyme.

To 0.95 ml of various buffer solutions having pH of about 6 to 10 containing 25% glycerol, 0.05 ml of 50 mM Tris-hydrochloride buffer (pH 7.5) containing 19.2 U of the enzyme was added. The mixtures were allowed to stand at 30° C. for 2 hours Then, 0.05 ml of each enzyme solution was added to 0.5 ml of D-α-alanineamide solution [50 mM phosphate buffer (pH 7.5) containing 12.5 g/l of D-α-alanineamide and 25% (v/v) glycerol], incubated at 37° C. for 30 minutes, and terminated by addition of 0.1 ml of 6N hydrochloric acid. The amount of D-α-alanine formed during the incubation was quantitatively determined. The enzyme activity was expressed in terms of relative activity, when defining the enzyme activity before standing at 30° C. for 2 hours as 100%. The results are shown in FIG. 3. As shown in FIG. 3, the enzyme was stable in a pH range of 6.5 to 10.

The temperature stability of the enzyme was determined by the following method.

Figure 4:
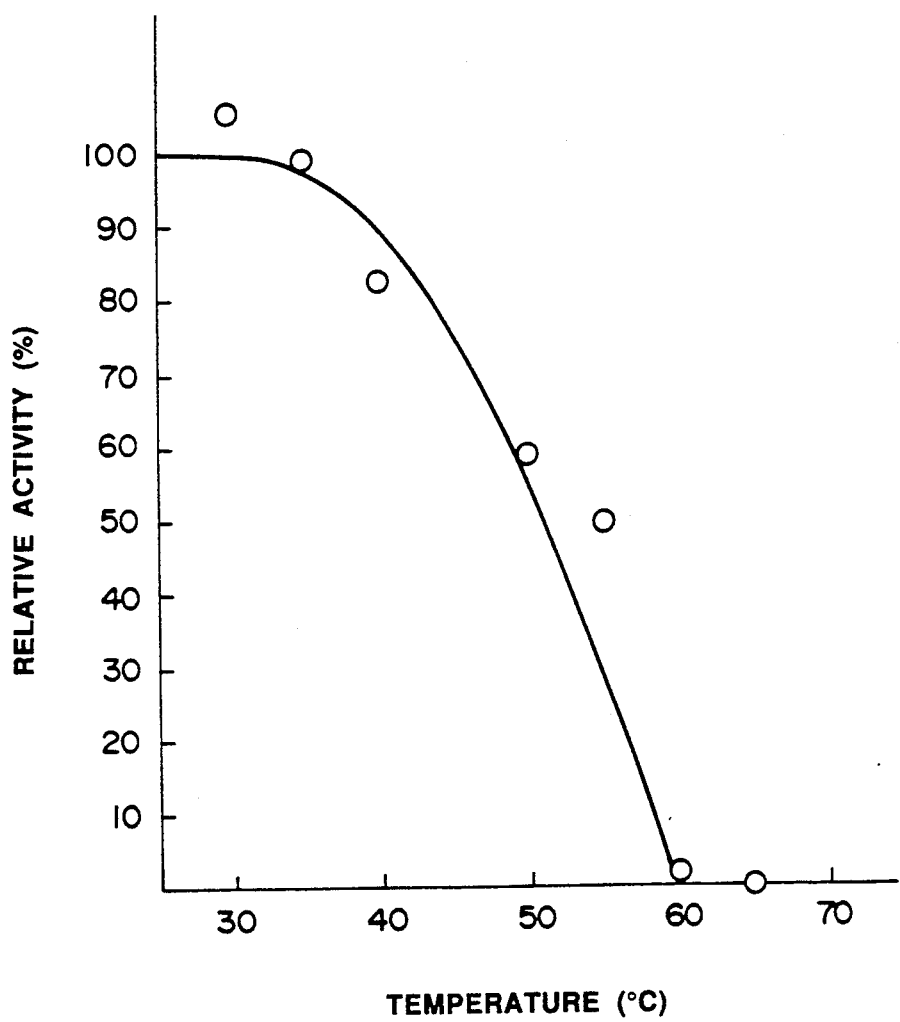
FIG. 4 shows the heat stability of the enzyme.

50 mM Tris-hydrochloride buffer (pH 7.5), 0.5 ml, containing 192 U of the enzyme was diluted to 10-fold with 50 mM phosphate buffer (pH 7.5) containing 25% glycerol. The diluted solution, 0.5 ml, was taken, allowed to stand for 10 minutes at various temperature, and immediately thereafter ice-cooled. To 0.5 ml of D-α-alanineamide solution [50 mM phosphate buffer (pH 7.5) containing 12.5 g/l of D-α-alanineamide and 25% (v/v) glycerol], 0.05 ml of the enzyme solution was added, incubated at 37° C. for 30 minutes, and terminated by addition of 0.1 ml of 6N hydrochloric acid. The amount of D-α-alanine formed during the incubation was quantitatively determined. The enzyme activity was expressed in terms of relative activity, when defining the enzyme activity before standing at various temperatures for 10 minutes as 100%. The results are shown in FIG. 4. As shown in FIG. 4, the enzyme was inactivated when allowed to stand for 10 minutes at temperatures above 60° C.

EXAMPLE 2

BYG medium (150 ml) having the same composition as in Example 1 was poured into each of 2 l-flasks provided with baffles, and sterilized at 120° C. for 20 minutes. Then, one loopful of Arthrobacter sp. H-4904 growing on a bouillon slant was inoculated into each of the media and cultured at 30° C. for 20 hours with shaking. The resulting culture was used as a seed culture.

Separately, a medium containing 3% of glucose, 2% of corn steep liquor, 0.5% of peptone, 1% of NaCl, 2% of $(NH_4)_2SO_4$, 0.3% of $MgSO_4.7H_2O$, 0.001% of $FeSO_4.7H_2O$, 0.0001% of $MnSO_4.7H_2O$ and 0.6% of DL-α-alanineamide and having a pH of 7.2 was prepared, and 1.5 l of the thus prepared medium was poured into a 3 l-jar fermenter and sterilized at 120° C. for 20 minutes. Then, 150 ml of the seed culture was aseptically introduced into the medium and cultured with agitation and aeration (800 rpm, 1 vvm) at 30° C. for 24 hours. The thus obtained culture was centrifuged at 4° C. for 10 minutes at 5,000 rpm. A solution containing 420 g of DL-α-alanineamide (592 g of hydrochloride thereof), 15.6 g of $NaH_2PO_4.2H_2O$ and 35.8 g of $Na_2HPO_4.12H_2O$ in deionized water was added to 10 g of the thus obtained wet cells to make the total volume of 2 l. The pH of the resulting mixture was adjusted to 6.7 with 10N NaOH. The hydrolysis reaction was carried out at 38° C. for 10 hours with gentle stirring. The mixture was kept at pH 6.7 with 6N HCl during the reaction.

After completion of the hydrolysis reaction, the amount of D-α-alanine and the amount of L-α-alanineamide in the reaction mixture were quantitatively determined. The results are shown in Table 2.

TABLE 2

|  | Titer (g/l) | Reaction yield (%) | Optical purity (%) |
|---|---|---|---|
| D-α-alanine | 105 | 99 | 99.3 |
| L-α-alanineamide | 105 | — | 99.0 |

Then 1 l of the reaction mixture was taken and the pH of the reaction mixture was adjusted to 4.5 and passed through a column packed with 3 l of Diaion SK1B ($NH_4^+$ form) (product of Mitsubishi Kasei Corporation) to separate D-α-alanine from L-α-alanineamide, and the respective fractions were crystallized through condensation under reduced pressure for precipitation, whereby 85 g of D-α-alanine (optical purity: 99.5% or higher) and 75 g of L-α-alanineamide (optical purity: 99.5% or higher) were obtained.

EXAMPLE 3

The hydrolysis reaction was carried out in the same manner as in Example 2 except that 210 g of D-α-alanineamide was used in place of DL-α-alanineamide.

As a result, 103 g/l D-α-alanine (optical purity: 99.1%) was formed and accumulated at the end of the reaction.

EXAMPLE 4

A desired mutant from Arthrobacter sp. H-4904 as the parent strain was obtained as follows.

The parent strain was cultured in an NB medium [a medium containing 20 g of bouillon powder (product of Kyokuto Co.) and 5 g of yeast extract (product of Difco Co.) in 1 l of water, adjusted to pH 7.2 with NaOH] at 30° C. for one day. The cells were recovered and suspended in a 0.1N Tris-maleic acid buffer solution (pH 6.0) at a concentration of $10^8$ cells/ml, and then 400 μg/ml N-methyl-N'-nitro-N-nitrosoguanidine (NTG) was added to the suspension. The suspension was incubated at room temperature for 30 minutes. The cells were thoroughly washed with physiological saline, smeared onto an NB agar medium (NB medium supplemented with 20 g of agar) and cultured at 30° C. for 1 to 6 days. The developing colonies were smeared on another NB agar medium and cultured at 30° C. for 1 to 2 days One loopful of the thus obtained strain was inoculated in a 250 ml-Erlenmeyer flask containing 40 ml of a BYG medium sterilized at 120° C. for 20 minutes and culturing was carried out at 30° C. for 21 hours with shaking. The thus obtained culture was centrifuged at 5,000 rpm for 10 minutes and the thus recovered cells were suspended in a 50 mM sodium phosphate buffer solution (pH 7.5) containing D-α-alanineamide hydrochloride to make a cell concentration of 2 g/l as wet cells. The D-α-alanineamide hydrochloride concentration was adjusted to make the final concentration of D-α-alanineamide of 25 g/l. After the reaction at 38° C. for one hour, the thus formed D-α-alanine was quantitatively determined through high performance liquid chromatography under the same conditions as in Example 1 to calculate the D-amidase activity per gram of the wet cells.

The D-amidase activity was expressed by units per gram of wet cell. Arthrobacter sp. H-4904 was used as control and cultured in the same manner as above except that 2 g/l DL-α-alanineamide was added to the medium, and the D-amidase activity was likewise determined.

In this manner, Arthrobacter sp. H-7095 was obtained as a mutant having the substantially same D-amidase activity as that of its parent strain, when cultured in a medium containing no inducing substance. The results are shown in Table 3.

TABLE 3

| Strains | DL-α-Alanineamide | D-amidase activity (U/g wet cells) |
|---|---|---|
| Arthrobacter sp. H-4904 | Added | 666 |
| Arthrobacter sp. H-7095 | None | 633 |

EXAMPLE 5

The hydrolytic reaction was carried out in the same manner as in Example 2, except that the cells of Arthrobacter sp. H-7095 were used which had been cultivated in a medium containing no DL-α-alanineamide.

The results are shown in Table 4.

TABLE 4

|  | Titer (g/l) | Reaction yield (%) | Optical purity (%) |
|---|---|---|---|
| D-α-alanine | 104 | 99 | 99.2 |
| L-α-alanineamide | 105 | — | 99.0 |

EXAMPLE 6

The hydrolytic reaction was carried out in the same manner as in Example 5, except that 210 g of D-α-alanineamide was used in place of DL-α-alanineamide. As a result, 104 g/l D-α-alanine (optical purity: 99.3%) was formed and accumulated at the end of reaction.

EXAMPLE 7

The culturing was carried out using Arthrobacter sp. H-7095 in the similar manner as in Example 5 to obtain 90 g of wet cells. The cells were washed with physiological saline and suspended in distilled water to make the total volume of 50 ml. A solution of 9 g of sodium arginate (Fuji Chemical Co., Ltd.) in 300 ml of distilled water was added to the suspension. The resulting mixture was dropwise added to 2% calcium chloride solution to give immobilized cells having a diameter of about 2 mm. Using the immobilized cells (25 g/l), the reaction was carried out in the same manner as in Example 2. As the result, 105 g/l D-α-alanine was formed and accumulated (optical purity: 98.2%).

EXAMPLE 8

The culturing was carried out using Arthrobacter sp. H-7095 in the similar manner as in Example 5 to obtain 50 g of wet cells. The cells were suspended in 10 mM phosphate buffer (pH 7.0) to make the total volume of 200 ml. The cells contained in the suspension were disrupted with a homogenizer (Nissei Excel, Autohomogenizer) at 15,000 rpm for 20 minutes under ice-cooling. The resulting suspension was centrifuged at 4° C. for 20 minutes at 12,000 rpm to give the supernatant as the cell extract. The supernatant (100 ml) was brought into contact with 20 ml of HPA-75 (product of Mitsubishi Kasei Corporation) which had been equilibrated with 10 mM phosphate buffer (pH 7.0) at 5° C. for 24 hours. To the suspension of HPA-75 was added 0.5% glutaraldehyde solution, and the mixture was incubated at 4° C. for 120 minutes to render HPA-75 crosslinked with D-amidase. Then, the mixture was washed 3 times with 10 mM phosphate buffer (pH 7.0) to give immobilized D-amidase. The specific activity of the immobilized product was 550 U/ml. Using the immobilized product (20 ml/l), the reaction was carried out in the similar manner as in Example 2. As a result, 104 g/l D-α-alanine was formed and accumulated (optical purity: 99.2%).

What is claimed is:

1. A process for producing at least one of D-α-alanine and L-α-alanineamide, which comprises carrying out an enzymatic hydrolysis in an aqueous medium containing DL-α-alanineamide in the presence of a culture, cells, or a treated product thereof, of a microorganism belonging to the genus Arthrobacter and capable of producing D-amidase having the following physicocochemical properties:
   a) activity and substrate specificity: it hydrolyzes D-α-alanineamide into D-α-alanine;
   b) optimum temperature: 40° to 45° C. at pH of 7.5;
   c) heat stability: inactivated at a temperature above 60° C. for 10 minutes;
   d) pH stability: stable within a range of pH 6.5 to 10.0 at 30° C.;
   e) molecular weight: 50,000±5,000 daltons by SDS-polyacrylamide electrophoresis;
   f) activation: no co-enzyme required for activation;
   g) isoelectric point: pH 5.2±0.3;
and recovering at least one of D-α-alanine and L-α-alanineamide from the resulting mixture.

2. The process according to claim 1, wherein the concentration of the cells is 1 to 50 g/l as wet cells.

3. The process of claim 1, wherein the concentration of D-α-alanineamide is 1 to 300 g/l.

4. The process of claim 1, wherein the concentration of DL-α-alanineamide is 1 to 500 g/l.

5. The process of claim 1, wherein the microorganism is Arthrobacter sp. H-4904 (FERM BP-1649).

6. The process of claim 1, wherein the microorganism is Arthrobacter sp. H-7095 (FERM BP-1773).

7. A process for producing D-amidase having the following physiocochemical properties:
   a) activity and substrate specificity: it hydrolyzes D-α-alanineamide into D-α-alanine;
   b) optimum temperature: 40° to 45° C. at Ph of 7.5;
   c) heat stability: inactivated at a temperature above 60° C. for 10 minutes; inactivated at a temperature above 60° C. for 10 minutes;
   d) pH stability: stable within a range of pH 6.5 to 10.0 at 30° C.;
   e) molecular weight: 50,000±5,000 daltons by SDS-polyacrylamide electrophoresis;
   f) activation; no co-enzyme required for activation;
   g) isoelectric point; pH 5.2±0.3;
said process comprises culturing a microorganism capable of producing D-amidase and belong to the genus Arthrobacter in an aqueous nutrient medium containing assimilable sources of carbon, nitrogen, and inorganic substances; and recovering said D-amidase.

8. The process according to claim 7, wherein the medium contains DL-α-alanineamide, D-α-alanineamide or L-α-alanineamide as an inducing substance.

9. The process according to claim 7, wherein D-amidase is recovered from cells in the culture.

10. The process of claims 7, 8 or 9, wherein the microorganism is Arthrobacter sp. H-4904 (FERM BP-1649).

11. The process according to any one of claims 7, 8 or 9, wherein the microorganism is Arthrobacter sp. H-7095 (FERM BP-1773).

12. A biologically pure culture of a microorganism of the genus Arthrobacter having all the identifying characteristics of Arthrobacter sp. H-4904 (FERM BP-1649).

13. A biologically pure culture of the microorganism of the genus Arthrobacter having all the identifying characteristics of Arthrobacter sp. H-7095 (FERM BP-1773).

* * * * *

UNITED STATES PATENT AND TRADEMARK OFFICE
CERTIFICATE OF CORRECTION

PATENT NO. : 5,130,240
DATED : July 14, 1992
INVENTOR(S) : AKIO OZAKI ET AL.

It is certified that error appears in the above-indentified patent and that said Letters Patent is hereby corrected as shown below:

COLUMN 12

Line 30, "belong" should read --belonging--.

Signed and Sealed this

Twenty-third Day of November, 1993

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,130,240
DATED : July 14, 1993
INVENTOR(S) : AKIO OZAKI, ET AL.

It is certified that error appears in the above-identified patent and that said Letters Patent is hereby corrected as shown below:

COLUMN 11

Line 42, "physicoco-" should read --physico- --.

COLUMN 12

Line 16, "physiocochemical" should read
　　　--physicochemical--.
　Line 19, "Ph" should read --pH--.
　Line 21, "inactivated at a temperature" should be deleted.
　Line 22 should be deleted.

Signed and Sealed this

Twenty-fifth Day of January, 1994

Attest:

BRUCE LEHMAN

Attesting Officer

Commissioner of Patents and Trademarks